United States Patent [19]

Vasquez

[11] Patent Number: 5,626,872
[45] Date of Patent: May 6, 1997

[54] PHARMACEUTICAL SOFT CAPSULES CONTAINING LYSINE CLONIXINATE AND A PROCESS FOR THEIR PREPARATION

[75] Inventor: Carlos E. M. Vàsquez, Buenos Aires, Argentina

[73] Assignee: Roemmers S.A.I.C.F., Argentina

[21] Appl. No.: 353,777

[22] Filed: Dec. 12, 1994

Related U.S. Application Data

[63] Continuation-in-part of Ser. No. 78,081, Jun. 16, 1993, abandoned.

[30] Foreign Application Priority Data

Jun. 16, 1992 [DE] Germany .................. 42 19 702.3

[51] Int. Cl.⁶ .................................................. A61K 9/48
[52] U.S. Cl. ........................ 424/451; 424/452; 424/456
[58] Field of Search ........................... 424/452, 451, 424/480, 461, 456

[56] References Cited

U.S. PATENT DOCUMENTS

| | | | |
|---|---|---|---|
| 3,973,027 | 8/1976 | Ferrari | 424/266 |
| 4,797,286 | 1/1989 | Thakkar et al. | 424/456 |
| 5,128,364 | 7/1992 | Girard et al. | 514/411 |
| 5,273,760 | 12/1993 | Oshlack et al. | 424/480 |
| 5,389,650 | 2/1995 | Frenette et al. | 514/337 |

FOREIGN PATENT DOCUMENTS

| | | | |
|---|---|---|---|
| 2253134 | 10/1976 | Germany | C07D 213/80 |
| 1374326 | 11/1974 | United Kingdom | C07C 101/54 |

*Primary Examiner*—Thurman K. Page
*Assistant Examiner*—William E. Benston, Jr.
*Attorney, Agent, or Firm*—Webb, Ziesenheim Bruening Logsdon Orkin & Hanson, P.C.

[57] ABSTRACT

A soft gelatin capsule with a filling including lysine clonixinate as an active ingredient and in a hydrophilic matrix and with a shell comprising gelatin, a plasticizer and sorbitol, wherein the plasticizer in many instances will be glycerol but may comprise the sorbitol alone. The presence of sorbitol in the gelatin capsule of a lysine clonixinate dosage form imparts unexpectedly good drug release and stability thereto.

12 Claims, No Drawings

PHARMACEUTICAL SOFT CAPSULES CONTAINING LYSINE CLONIXINATE AND A PROCESS FOR THEIR PREPARATION

This application is a CIP of Ser. No. 08/078,081 abandoned Jun. 6, 1993.

The present invention relates to a pharmaceutical composition for oral administration containing as active ingredient the analgesic and anti-inflammatory agent lysine clonixinate. The invention also concerns a process for the preparation of soft capsules that comprise lysine clonixinate. Moreover the invention relates to the use (method of treatment) of lysine clonixinate in capsules for the treatment of pain and inflammatous conditions.

The L-lysine salt of 2-[(3-chloro-2-methylphenyl)amino]-3-pyridine carboxylic acid, or lysine clonixinate, is described in patent specifications DE 2.253.134 and U.S. Pat. No. 3,973,027. In both of these specifications there is reference to formulations for oral, parenteral and rectal administration.

Oral administration constitutes a preferred route for administering lysine clonixinate, but tablets are the only type of formulation known in the art and existing in the market. However, it has been observed that the administration of lysine clonixinate in the forms of solid tablets—or of powder filled, hard shell capsules—present the problem of inducing some local erosion in the digestive tract. On the other hand, the time of onset of the therapeutic action following oral administration of the drug is an important consideration: It is highly desirable from the patient's point of view that the drug begin to relieve pain or inflammation as quickly as possible. Therefore, the development of an oral pharmaceutical formulation of lysine clonixinate that provides more rapid therapeutic onset and less discomfort would be interesting.

Alternative to powder-filled hard-shell capsules or tablets for the oral administration of pharmaceuticals, vitamins, dietary supplements and the like. These soft capsules are often preferred by patients since they are easier to swallow than conventional hard capsules or tablets.

With a highly water soluble compound, as lysine clonixinate is, a soft gelatin capsule formulation faces the problem of embrittlement of the shell, with the corresponding leaking of the fill material. The prevention of the oxidation of the lysine clonixinate in a filling in the form of solution or dispersion constitutes an extra problem in this case.

It is known from "Pharmaceutics: The Science of Dosage Form Design", Churchill Linvingstone, Edinburgh 1988, pages 332–337, edited by Michael E. Aulton, that soft gelatin capsules can be obtained by utilizing gelatin together with glycerol as plasticizer. In general the greater the plasticizer content, the greater the flexibility of the shell will be. There is, however, no recognition that a plasticizer as such could prevent a solubilised drug to wander around and concentrate in the shell of the capsule where such drug can cause irritations to a patient.

It is an object of the present invention to provide soft gelatin capsules containing an effective unit dosage amount of lysine clonixinate, said capsules being stable during a long time, easy to manufacture with the standard machinery, and providing rapid onset of the therapeutic activity upon oral administration of the capsule, with less harmful side-effects than the lysine clonixinate tablets currently in the market.

It is a further object of the invention to provide a soft gelatin capsule containing lysine clonixinate wherein migration of lysine clonixinate to the shell is reduced or prevented. Conventional shells have the drawback that due to the bitter taste of lysine clonixinate irritations during swallowing of these capsules occur.

SUMMARY OF THE INVENTION

I have developed a pharmaceutical dosage unit form of a soft gelatin capsule with a filling including lysine clonixinate as an active ingredient and in a hydrophilic matrix and with a shell comprising gelatin, a plasticizer and sorbitol. In most instances glycerol is used as plasticizer. However, the plasticizer may solely comprise sorbitol.

In a preferred embodiment the shell consists of 30 to 70 percent by weight gelatin, generally a plasticizer and 50 to 10% by weight sorbitol. It is preferred that the shell includes 10 to 35% by weight sorbitol, most preferred 12 to 20% by weight sorbitol. It is understood that the term percent by weight in this context refers to the weight of the shell.

The filling of the soft gelatin capsule is liquid and includes apart from lysine clonixinate as an active ingredient a hydrophilic matrix. Typically such hydrophilic matrix comprises polyethylene glycol having an average molecular weight of from about 200 to 1000. Further ingredients are water and optionally thickening agents. It is preferred that the hydrophilic matrix includes polyethylene glycol having an average molecular weight of from about 200 to 1000, 3 to 10% by weight of glycerol, and 5 to 15% by weight of water. The polyethylene glycol can be mixed with propylene glycol and/or propylene carbonate.

The term "liquid filling" in the sense of the present invention means that the filling is liquid under ambient conditions. This term, however, includes that the filling may be present as a gel. The crucial condition thus far is that the lysine clonixinate is provided in the form of a solution as opposed to a suspension or powdery formulation. In the latter case the advantages of the present invention would be diminished since the lysine clonixinate would not be as quickly released to the digestive tract.

An embodiment of the present invention is a pharmaceutical dosage unit form of the type soft gelatin capsule with a filling comprising lysine clonixinate as active ingredient, said filling being based on a hydrophilic matrix comprising polyethylene glycol having an average molecular weight of from about 200 to 1000, or a mixture of the polyethylene glycol with propylene glycol and/or propylene carbonate, glycerol in 3 to 10% by weight, and water in 5 to 15% by weight (all concentration values relate to the filling).

The recommended contents of lysine clonixinate per dosage unit is from 20 to 300 mg, preferably 125 mg. The preferred polyethylene glycol has an average molecular weight of about 400.

Instead of polyethylene glycol, propylene glycol or propylene carbonate may be utilized.

The capsule filling may if desired contain additional ingredients such as preservatives, flavouring and/or sweetening agents. Lysine clonixinate is kept virtually dissolved in the filling and it is quickly released to the digestive tract when the capsule shell dissolves.

A further embodiment of the invention is a filling comprising lysine clonixinate as active ingredient in a hydrophilic matrix of the type described above.

According to the invention a pharmaceutical dosage unit is provided with lysine clonixinate as active ingredient, comprising a soft gelatine capsule as described above, with a content of lysine clonixinate of 20 mg to 300 mg, preferably 125 mg.

Anther embodiment according to the invention is a process for the preparation of soft gelatine capsules with a filling comprising lysine clonixinate as active ingredient comprising the simultaneous or successive steps:
(a) forming the gelatine capsules, and
(b) filling the capsules with lysine clonixinate as active ingredient, a hydrophilic matrix comprising polyethylene glycol having an average molecular weight of from about 200 to 1000 or a mixture of said polyethylene glycol with propylene glycol and/or propylene carbonate, glycerol in 3 to 10% by weight, and water in 5 to 15% by weight (all concentration values relate to the filling).

A further embodiment according to the invention is the method of treatment of the above mentioned capsules as analgetics or anti-inflammatory agents.

The filling of the present invention is to be used with the soft gelatin capsule shell as set forth above. In one shell formulation, there is included about 30-35 parts by weight of gelatin, about 5-20 parts by weight of a plasticiser, such as glycerol or sorbitol, at least 10 parts by weight sorbitol and about 16-40 parts by weight of water. Additionally, the gelatin shell may contain preservatives, such as mixed parabenes in minor proportions. In a conventional manner, the gelatin composition is mixed and melted under vacuum conditions. The capsules may be simultaneously formed and filled using conventional methods and apparatus. The gelatin capsules are formed into the desired shape and size so that they can be readily swallowed, usually with the aid of water. The resulting capsule is soluble in water and in gastrointestinal juices.

The interval of average molecular weight (from about 200 to 1000) for the polyethylene glycol used in the filling of the present invention is crucial, because polyethylene glycols of much lower molecular weight tend to diffuse through the shells of conventional soft gelatin capsules. In turn, the use of polyethylene glycols with higher molecular weight tends to result in a too viscous, unpumpable vehicle, difficult to manufacture by ordinary machinery.

The contents of glycerol (3-10%) and water (5-15%) in the filling corresponding to the dosage units of the present invention are crucial to reduce any undesirable interaction between the polyethylene glycol and the soft gelatin shell. Glycerol and water act as humectants by setting up a sort of equilibrium between the moisture content of the filling and the soft gelatin capsule shell. Similarly, glycerol acts as equilibrium plasticiser so that the polyethylene glycol does not remove excessive amounts of plasticisers from the soft gelatin capsule shell. Thus, water and glycerol prevent the polyethylene glycol from rendering the soft gelatin capsule hard, brittle, and subject to damage and leaking during handling. Preferred filling compositions according to the present invention are those of Example 1.

The fact that lysine clonixinate is kept in solution in the filling of the capsules, and therefore it is quickly released to the digestive tract when the shell dissolves, gives the capsules of the present invention a higher bioavailability than that of the corresponding tablets known in the art. This feature, which is illustrated by the pharmacokinetic results of Example 2, represents a more rapid therapeutic onset for the patient, and therefore an advantage over the current tablets in the market.

The administration of the dosage unit forms of the present invention has another advantage: When the shell dissolves, lysine clonixinate diffuses very quickly in its environment. Thus, local erosion—and its associated damage or discomfort—is smaller than with the current tablets.

Capsules of the present invention have been easily prepared with standard machinery and have proved stable for more than a year under high humidity conditions, as illustrated in the accompanying Example 3.

EXAMPLE 1

Preparation of Soft Gelatin Capsules of Lysine Clonixinate

Two fill materials having the compositions per capsule shown in Table 1 were prepared. The fill materials were thoroughly mixed under nitrogen atmosphere, and they were encapsulated in conventional soft gelatin shells. The fill materials proved to be nondilatant and compatible with conventional soft gelatin capsule manufacturing processes, such as those disclosed, for example, in U.S. Pat. No. 2,288,327 and U.S. Pat. No. 2,318,718. Besides, the gelled fill materials were temperature stable and did not remove excessive amounts of water or plasticisers from the soft elastic gelatin shell.

TABLE 1

| Typical capsule filling compositions (in mg/capsule) | | |
|---|---|---|
| Ingredients | Filling A | Filling B |
| lysine clonixinate | 125 | 125 |
| polyethylene glycol 400 | 344 | 293 |
| anhydrous glycerol | 35 | 31 |
| water | 56 | 50 |

EXAMPLE 2

Pharmacokinetics Comparative Test Between Soft Gelatin Capsules and Tablets of Lysine Clonixinate A conventional pharmacokinetics comparative study was carried out with 28 healthy fasting human volunteers. Fourteen of them received a single 125 mg dose of commercially available lysine clonixinate tablets, whereas the other 14 received the same dose in the form of soft gelatin capsules with the filling composition A of Table 1. The obtained pharmacokinetic results are those shown in Table 2.

TABLE 2

| Pharmacokinetic parameters of two pharmaceutical forms | | |
|---|---|---|
| Parameter | Gelatine Capsules | Tablets |
| $t_{1/2}$ (h) | 0.17 | 0.29 |
| $t_{max}$ (h) | 0.5 | 1.0 |
| AUC (µg/h/ml) | 10.36 | 10.09 |
| $C_{max}$ (µg/ml) | 4.8 | 5.6 |

Notes: $t_{1/2}$ = half life; $t_{max}$ = time at which $C_{max}$ is attained; AUC = Area Under Curve; $C_{max}$ = maximum Concentration.

EXAMPLE 3

Stability Test of Soft Gelatin Capsules of Lysine Clonixinate

The stability of the two soft gelatin capsules prepared according to Example 1 were studied over a period of 36 months, in conditions of 20°-25° C. and 50-70% relative humidity. It was observed that the capsules were stable, without signs of embrittlement, and that the active ingredient was not altered, e.g. by oxidation.

I have discovered that soft gelatin shells obtained according to conventional wisdom have significant drawbacks (cf. the following comparison examples). In particular, such soft gelatin capsules have a bitter taste due to lysine clonixinate which has diffused from the filling to the shell. Such bitter taste causes irritation to patients and in particular younger patients may even refuse to swallow such capsule. More important, such capsules darken after a short time. This darkening is caused by the oxidation of lysine clonixinate which in conventional capsules will be exposed at the surface of said capsule to the ambient.

COMPARATIVE EXAMPLE I

A conventional soft gelatin capsule was prepared on the basis of the following percentages:

| Shell | |
|---|---|
| gelatin | 73.7% |
| anhydrous glycerol | 17.3% |
| water | 9.0% |
| Filling | |
| lysine clonixinate | 25% |
| polyethlene glycol | 75% |

It was observed that 5 to 10% of the lysine clonixinate migrated into the shell. Moreover the capsules collapsed after 6 month of storage. Furthermore, a delay in the dissolution of the capsules was observed.

COMPARATIVE EXAMPLE II

In a further attempt to provide capsules fullfilling the practical needs soft gelatin capsules according to the following were prepared:

| Shell | |
|---|---|
| gelatin | 73.7.% |
| anhydrous glycerol | 17.3% |
| water | 9% |
| Filling | |
| lysine clonixinate | 25% |
| anhydrous glycerol | 5% |
| water | 8% |
| polyethylene glycol | 62% |

The obtained capsules remain stabile even after 6 month of storage. However, still then the drug migrated into the shell and the lysine clonixinate contents of the filling was degraded by oxidation.

EXAMPLE 4

The soft gelatin capsule according to the present invention was prepared according to the following:

| Shell | |
|---|---|
| gelatin | 57.9% |
| anhydrous glycerol | 17.3% |
| water | 9.0% |
| sorbitol | 15.8% |

-continued

| Filling | |
|---|---|
| lysine clonixinate | 25% |
| unhydrous glycerol | 5% |
| water | 8% |
| polyethylene glycol | 62% |

Surprisingly it was found that even after 6 month of storage the soft gelatin capsules did not exhibit a trace of a bitter taste. No degradation by oxidation at the shell surface could be observed. Moreover, the capsules remained stabile.

I claim:

1. A pharmaceutical dosage unit form of the type soft gelatin capsule with a filling comprising lysine clonixinate as active ingredient, said filling being based on a hydrophilic matrix comprising polyethylene glycol having an average molecular weight of from about 200 to 1000, or a mixture of the polyethylene glycol with propylene glycol and/or propylen carbonate, glycerol in 3 to 10% by weight and water in 5 to 15% by weight, and with a shell comprising about 30 to 70% by weight gelatin and a plasticizer, wherein the improvements is that said shell includes 50 to 10% by weight sorbitol.

2. The soft gelatin capsule of claim 1 wherein said shell includes 10 to 35% by weight sorbitol.

3. The soft gelatin capsule of claim 2 wherein said shell includes 12 to 20% by weight sorbitol.

4. The soft gelatin capsule of claim 1 including lysine clonixinate in an amount of from 20 to 300 mg.

5. The soft gelatin capsule of claim 4 comprising lysine clonixinate in an amount of about 125 mg.

6. The soft gelatin capsule of claim 1 wherein the hydrophilic matrix comprises polyethylene, glycol having an average molecular weight of from about 200 to 1000.

7. The soft gelatin capsule of claim 6 wherein the polyethylene glycol has an average molecular weight of about 400.

8. The soft gelatin capsule of claim 6 further including propylene glycol mixed with said polyethylene glycol.

9. The soft gelatin capsule of claim 6 further including propylene carbonate mixed with said polyethylene glycol.

10. The soft gelatin capsule of claim 6 further including propylene glycol and propylene carbonate mixed with said polyethylene glycol.

11. A process for the preparation of a soft gelatin capsule with a filling comprising lysine clonixinate, comprising the steps of (A) forming gelatin capsules consisting essentially of gelatin, a plasticizer and sorbitol, and (B) filling the capsules with lysine clonixinate as an active ingredient, a hydrophilic matrix comprising polyethylene glycol having an average molecular weight of from about 200 to 1000, or a mixture of said polyethylene glycol with propylene glycol and/or propylene carbonate, glycerol in 3 to 10% by weight, and water in 5 to 15% by weight.

12. Method of treatment of pain and inflammation comprising administering the soft gelatin capsule of claim 1.

* * * * *